United States Patent [19]

Hall

[11] 4,081,326

[45] Mar. 28, 1978

[54] METHOD FOR REMOVING MALTOTETRAOSE AND LOWER SACCHARIDES FROM SOLUTION

[75] Inventor: Leo M. Hall, Homewood, Ala.

[73] Assignee: The Board of Trustees of the University of Alabama, Birmingham, Ala.

[21] Appl. No.: 730,820

[22] Filed: Oct. 7, 1976

[51] Int. Cl.$^2$ .............................................. C12D 13/02
[52] U.S. Cl. ......................................... 195/7; 195/11; 195/31 R; 195/99; 195/103.5 R
[58] Field of Search ....................... 195/4, 7, 11, 31 R, 195/111, 13, 62, 66 R, 65, 99, 103.5 R; 127/29

[56] References Cited

U.S. PATENT DOCUMENTS

| 3,654,082 | 4/1972 | Abdullah | 195/31 R |
| 3,788,910 | 1/1974 | Stewart et al. | 195/11 |
| 3,804,716 | 4/1974 | Langlois | 195/31 R |

OTHER PUBLICATIONS

Chiba et al., "Substrate Specificity of Saccharomyces logos α-Glucosidase", *Agr. Biol. Chem.*, vol. 37, No. 8, (1973) pp. 1831-1836.

Halvorson et al., "Comparison of the α-Glucosidases of Saccharomyces Produced in Response to Five Non-Allelic Maltose Genes", Biochim. Biophys. Acta vol. 67 (1963), pp. 42-53.

Whelan et al., "The Mechanism of Carbohydrase Action, PartI. the Preparation and Properties of Maltodextrin Substrates", Journal Chem. Soc., Apr. (1953), pp. 1293-1298.

*Primary Examiner*—Alvin E. Tanenholtz
*Assistant Examiner*—Thomas G. Wiseman
*Attorney, Agent, or Firm*—Oblon, Fisher, Spivak, McClelland & Maier

[57] ABSTRACT

An oligosaccharide fraction containing essentially no $G_4$ and increased amounts of $G_5$, $G_6$ and $G_7$, is prepared by simultaneously treating a solution containing the desired oligosaccharides with both a baker's yeast and a maltase.

15 Claims, No Drawings

METHOD FOR REMOVING MALTOTETRAOSE AND LOWER SACCHARIDES FROM SOLUTION

BACKGROUND OF THE INVENTION

1. Field of the Invention

The present invention relates to a method for preparing an oligosaccharide fraction. More particularly, it relates to a method for extracting a suitable molecular weight range of oligosaccharides for use, for example, as a substrate for amylase assay.

2. Description of the Prior Art

Heretofore, many processes for preparing maltooligosaccharides have been used. Generally, these involve chromatographic separation by such techniques as partition column chromatography on cellulose, adsorption chromatography on charcoal and exclusion chromatography on polyacrylamide gels or dextran gels. (Whistler et al, JACS 77, 5761 (1955); Whelan et al, *Biochem. J.* 58, 569 (1954); Whistler et al, *JACS* 77, 1017 (1955); French et al, *JACS* 71, 356 (1949); Trenel et al, *J. Chrom.* 42, 476 (1969); Whistler et al, *JACS* 72, 677 (1950); Hough et al, *J. Chem. Soc.* 2511 (1949)) In all of these methods the presence of large amounts of glucose, maltose ($G_2$) and maltotriose ($G_3$) severly limits the amount of material that can be fractionated.

Other methods utilize a combination of a fermentation step followed by a chromatographic separation. For example, in U.S. Pat. No. 3,788,910, a brewer's wort is fermented with a yeast to remove sugars of lower molecular weight than those desired. After the yeast is removed, the desired maltotriose/maltotetraose fraction is collected by gel filtration chromatography.

Similarly, studies have shown that commercial baker's yeast is capable of completely removing glucose, maltose and maltotriose but not oligosaccharides of higher weight. Fractionation by column chromatography is required to remove the lower unwanted oligosaccharides such as $G_4$ and $G_5$. However, this general method is not very amenable to commercial preparation of large quantities of oligosaccharide fractions of higher molecular weight, such as from about maltopentaose ($G_5$) to about maltodecaose ($G_{10}$). Moreover, since fractionation by column chromatography is required, it is expensive and time consuming.

Because of this inability to prepare oligosaccharides in a commercially feasible and technically acceptable fashion, significant improvements in several analytical systems, which would be possible if such substrates were available, have been prevented. For example, a conventional system for amylase assay incorporates the following reactions:

1. Starch, glycogen or maltodextrin (substrate) $\xrightarrow{\text{amylase}}$ maltose + smaller oligosaccharides 2. Maltose $\xrightarrow{\text{maltase}}$ glucose 3. Glucose + ATP $\xrightarrow{\text{hexokinase}}$ glucose-6-phosphate + ADP 4. Glucose-6-phosphate + NAD $\xrightarrow{\text{glucose-6-phosphate dehydrogenase}}$ 6-phosphogluconolactone + NADH The rate of formation of NADH, once zero-order kinetics is established for equation (4), is directly proportional to the amount of amylase present in the sample. NADH is monitored spectrophotometrically by its absorbance at 340 nm.

However, the use of polymeric oligosaccharides such as starch has the distinct disadvantage that a considerable lag is observed before the indicator reaction (Reaction 4) shows zero-order kinetics. Another disadvantage is the relatively low sensitivity of the resultant amylase determination since the hydrolysis of large polymeric oligosaccharides produces many other smaller oligosaccharides rather than predominantly maltose, maltotriose or maltotetraose, which are readily hydrolyzed to glucose by the maltase in Reaction 2, as required. Thus, amylase can cleave several glycosidic bonds in these large polymeric oligosaccharides but no indication of amylase activity will be observed until a proper substrate for maltase activity is produced (Reaction 2). The use of substrates of smaller oligosaccharides which are not hydrolyzed by maltase, such as maltopentaose, maltohexaose, maltoheptaose, maltooctaose, maltononaose or mixtures of these substrates would increase the sensitivity of the test as well as reduce the time required to reach zero-order kinetics of the indicator reaction (Reaction 4), thereby significantly improving the conventional assay. Ideally, pure $G_5$ would be the preferred substrate since only one $G_2$ could be produced per glucosidic bond severance, but its cost of production would be commercially prohibitive. The use of the mixture described above, however, would give analytical values for amylase comparable to those obtained if pure $G_5$ alone were used.

SUMMARY OF THE INVENTION

Accordingly, it is an object of this invention to provide a method for preparing large quantities of oligosaccharides in high purity.

It is another object of this invention to provide such a process which does not require a chromatographic step for fractional separation of oligosaccharides.

It is still another object of this invention to provide a process for preparing oligosaccharides which are suitable as substrates in amylase assay systems.

It is further an object of this invention to provide a process for preparing an oligosaccharide fraction containing substantially no maltooligosaccharides having a molecular weight of less than $G_5$.

Briefly, these and other objects of this invention as will hereinafter be made clear have been attained by providing a method for preparing an oligosaccharide fraction which comprises removing substantially all oligosaccharides below a desired minimum molecular weight from a sample containing a mixture of oligosaccharides by simultaneously treating the sample with a yeast and a maltase.

DETAILED DESCRIPTION OF THE PREFERRED EMBODIMENTS

The present invention is based upon the discovery of a synergistic effect occurring when an oligosaccharide-containing solution is simultaneously treated with both a yeast and a maltase. When such a solution is fermented with the yeast alone, only $G_1 - G_3$ oligosaccharides are removed. Similarly, when maltase is used alone, only $G_2$ and $G_3$ are significantly hydrolyzed. If the remaining oligosaccharides were used, for example, as an amylase assay substrate, $G_4$ would typically be hydrolyzed by the maltase in the assay reagent thereby providing non-amylase-produced glucose for detection. However, when the yeast and the maltase are present simultaneously in the oligosaccharide-containing sample, maltotetraose ($G_4$) is removed and the relative concentrations of $G_5$, $G_6$ and $G_7$ are increased such that the resulting oligosaccharide mixture forms an excellent substrate for an amylase assay. Most significantly, this result is achieved without the need for any fractional column chromatography for removing lower weight oligosaccharides. This is a completely unexpected result.

While the mechanism of the synergism is not fully understood, it is theorized that the maltase alone will not hydrolyze $G_4$ present in the starting solution, such as corn syrup, because the presence of glucose in high concentrations in the syrup inhibits the maltase enzyme activity. Thus, an oligosaccharide substrate produced by the action of maltase alone and followed by removal or inactivitation of the maltase prior to treatment with yeast would yield a product containing large amounts of $G_4$. However, the simultaneous presence of a viable yeast and an active maltase results in the removal of glucose as it is formed which permits removal of $G_4$ by maltase. Thus, the process can be carried out either by
1. fermenting the corn syrup with yeast alone followed by the addition of maltase; or
2. adding the maltase alone followed by the addition of yeast.

The critical and novel feature is the simultaneous presence of viable yeast and active maltase at one stage of the preparation. However, other techniques of removing glucose from the maltase-containing solutions can also be used to achieve $G_4$ removal by the maltase.

The source of the oligosaccharide-containing sample is not critical. Generally, natural extracts derived from enzymatic conversion or acid hydrolysis of starch-containing materials, such as grains or tubers such as potato starch, into the larger sugars are suitable sources. These include corn syrup, brewer's wort, corn steep liquor, barley malt extract and the like. Corn syrup is preferred since it has a very high content (20-45%) of oligosaccharides in the desired range from about $G_5$ to about $G_{10}$. Typically, corn syrup should have a degree of polymerization (D.P.) in the range of 8-40, preferably 10-15, since the oligosaccharide contents are higher. An oligosaccharide-containing solution suitable for use in this invention can be prepared by dissolving approximately 0.2 to 2.5 kg, preferably 1.9 - 2.1 kg, of corn syrup in 4.5 to 7.0 liters, preferably 5.5 to 6.0 liters, of $H_2O$.

The yeast used in this invention may be, in general, a species of Saccharomyces, e.g. *S. cerevisiae, S. italicus* or *S. uvarum*. Any strain of baker's yeast should be usable. A convenient source of such a yeast is commercial baker's yeast, e.g., Fleischman or Red Star TM. The only requirement is that the yeast be able to ferment maltose and glucose and not be able to ferment $G_5$, $G_6$, $G_7$ etc. to any significant extent and, of course, that it be uncontaminated with fungus. The amount of yeast required is an amount effective to ferment the maltose and glucose, preferably in 18 to 36 hours. Generally, from .0075 to 0.20 kg, preferably from 0.05 to .10 kg of yeast per 1.0 liter of oligosaccharide-containing solution should be added.

The maltases (α-glucosidase) suitable for use in the invention include those having a specificity such that maltotetraose ($G_4$) is hydrolyzed to maltose or to maltotriose and glucose, and in addition that $G_5$, $G_6$, $G_7$, $G_8$ etc. and higher oligosaccharides are not significantly hydrolyzed. If the yeast strain used in the preparation is not able to ferment maltotriose, then the maltase must also be able to hydrolyze $G_3$. Maltases obtained from *Saccharomyces cerevisiae*, and from *Saccharomyces italicus*, for example, are usable; while those from *Saccharomyces uvarum* or molds such as *Aspergillus niger* are not suitable. Particularly preferred is a specific maltase isolated from a strain of brewer's yeast (Hallstrain) as disclosed in copending U.S. application Ser. No. 742,240, filed Nov. 16, 1976, which is incorporated by reference herein. The maltase of this copending application, suitable for use in this invention is that labelled "Peak II maltase". Details of its properties and preparations may be found in the referenced application. The amount of maltase required is a catalytic amount, i.e., that sufficient for catalyzing the hydrolysis of oligosaccharides. Generally, from 300,000 to 2,000,000.00 preferably from 800,000 to 1,200,000, units per liter of oligosaccharide solution and from 0.0075 to 0.20, preferably from 0.05 to 0.10 kg of yeast should be added per liter. A unit of maltase activity is defined as the amount of enzyme giving rise to an absorbance change of 1.00/min in a 1.00 cm cell containing 1.0 ml of p-nitrophenyl-α-D-glucoside (0.20 mg/ml) in 0.10 M potassium phosphate buffer; 400 nm; 38° C, pH 6.80. The required purity is such that α- or β-amylase activity be absent from the maltase preparation.

The order of addition of the yeast and maltase is not at all critical. Either may be added first or both may be added together. In either of the first two cases, $G_2$–$G_3$ only are hydrolyzed until the other component is added. Thereafter, by synergistic action of the yeast and the maltase, $G_4$ is hydrolyzed relatively rapidly and $G_5$ only slowly. The time between addition of the components is also not critical. The preferred order of addition is to add the yeast first and then to add the maltase later. The preferred time of fermentation with yeast alone is 18–40 hours, preferably 34 to 38 hours. There is no advantage in adding the maltase first, but it can be done if the total time of fermentation is increased by 36 to 48 hours. Thus, a disadvantage of adding the maltase first and then the yeast hours later is that the total process is lengthened and the maltase enzyme is slowly inactivated, requiring a longer time of preparation to remove $G_4$ or necessitating further addition of maltase after the yeast is added. However, with the preferred amounts of yeast and maltase given, the order of addition is not critical and suitable substrate can be obtained by either sequence. From the point at which the yeast and maltase are simultaneously present in the oligosaccharide-containing solution, generally from 36-72 hours are sufficient to remove malotetraose. Final contamination with glucose, maltase, maltotriose and maltotetraose is insignificant.

During the treatment with the yeast alone, the temperature of the oligosaccharide-containing solution should be maintained at from 25° to 35° C, preferably from 29° to 32° C, and the pH at from 6.0 to 7.5, preferably from 6.4 to 6.8. For maltase treatment alone the temperature should be from 25 to 32° C, preferably from 28° to 31° C, and the pH from 6.0 to 7.5, preferably from 6.4 to 6.8. During the simultaneous treatment with yeast and maltase the pH range is 6.0 to 7.2, preferably 6.4 to 6.8. The temperature range is 25° to 32° C, preferably 29°–32° C. The pH can be maintained by the addition of either KOH or NaOH pellets or solutions. In all cases, the yeast is slowly stirred to keep it in suspension throughout the treatment. Vigorous stirring or aeration is to be avoided because denaturation of the maltase enzyme can result. From 0.2 to 0.4 g, preferably from 0.3 to 0.35 g, of sodium azide per liter of solution should also be added to prevent bacterial growth. It is also preferred to add orthophosphoric acid in a form such as $KH_2PO_4$, which is preferred, $K_3PO_4$, $NaH_2PO_4$, $Na_2HPO_4$, $(NH_4)_2HPO_4$, $Na_3PO_4$, or $H_3PO_4$ to serve as a buffer to avoid rapid fluctuations in the pH and also to stimulate the yeast fermentation as is conventional. A suitable range of this additive is from 0.0 to 12 gm of $KH_2PO_4$ per liter, preferably 6.0 to 7.0 gm per liter or equivalent amounts of the other forms.

After completion of the desired hydrolysis, generally after 72–120 hours of the simultaneous presence of the yeast and the maltase, the fermentation mixture may be treated by any conventional method which is effective to denature the maltase and to remove the yeast. When maltase is not completely denatured, maltose and maltotriose accumulate in the solution of the oligosaccharide. A preferred method is as follows:

1. The pH of the mixture is adjusted to 2.0–4.0 with the addition of hydrochloric acid.
2. The mixture is heated rapidly to 70°–75° C (the total time to reach 70° C is not critical — approximately 20 minutes is convenient), and cooled to from 0° to 25° C.
3. A filter aid is added (e.g., Celite ®) and the mixture filtered to remove the yeast and the denatured protein in conventional fashion.

The clear pale yellow filtrate which results may be lyophilized and used directly as a substrate in amylase assay. However, it is preferred to remove phosphates and other salts and to clarify the solution by passage of the filtrate through an adequate amount of conventional mixed-bed ion-exchange resin, such as Amberlite MB-3 or HN-High Capacity Hose Nipple Cartridge D8901 (Barnstead Company), and then to lyophilize the effluent to remove the ethanol produced during fermentation.

Yields are approximately 700–900 grams of substrate for a typical 2 kg sample of corn syrup. This represents an extracting yield of about 35–45% for $G_6$ and higher weight oligosaccharides.

Of course, additional treatments are not excluded by the method of this invention. For example, the oligosaccharide-containing sample may be pretreated with a conventional ethanol solution for removal of unwanted larger oligosaccharides and dextrins. Alternatively, this ethanol treatment may be effected after removal of the yeast and the denatured maltase. Other conventional pretreatments can also be performed such as dialysis to remove some of the lower molecular weight oligosaccharides. Moreover, although a significant feature of this invention is the elimination of the need for a fractionating chromatography step, such an additional treatment is not precluded. The effects of such a chromatographic separation can be both beneficial and detrimental. In view of the time, complexity and, most importantly, the cost involved in utilization of such an extra step on an industrial scale, further separation on a column is strongly contraindicated. In any event, such a step is clearly not required, but when desired is fully compatible with the present process.

Having generally described the invention, a more complete understanding can be obtained by reference to certain specific examples, which are included for purposes of illustration only and are not intended to be limiting unless otherwise specified.

In the Examples, the materials and analytical techniques used were as follows. Detection of Oligosaccharides by TLC: The procedures used were slight modifications of the published procedures by Mansfield, in Quantitative Thin Layer Chromatography, edited by Touchstone, J.C., John Wiley and Sons, New York, 1973, pp. 79–93. Plates were routinely scanned with a Schoeffel Spectrodensitometer. Relative concentrations of oligosaccharides were calculated from the peak height of the various oligosaccharide spots on the densitometer scan.

Yeast: Commercially available baker's yeast.

Corn syrup: That used in all studies was a sample of #1033 corn syrup obtained from Corn Products International.

Maltase: The maltase was prepared from the Hall strain of yeast according to the above-identified copending application.

Determination of Blank Rate and Sensitivity of Substrate in Amylase Assay: The measurement of the blank rate and sensitivity of the substrate in the amylase assay system was determined after the addition of suitable amounts of substrate dissolved in $H_2O$ (final concentration of oligosaccharide was 3.0 mg/ml) to a lyophilized reagent reconstituted with $H_2O$. The final concentration of components in the assay cuvette (1.00 ml final volume; light path 1.00cm) were as follows:

| | |
|---|---|
| Potassium phosphate buffer, pH 6.8 | 0.10 M |
| NaCl | 0.05 M |
| $Na_2ATP \cdot 3H_2O$ | 2.0 mg/ml |
| NAD | 1.0 mg/ml |
| Magnesium acetate | 0.01 M |
| Hexokinase | 3.0 IU/ml |
| Glucose-6-P dehydrogenase | 4.0 IU/ml |
| Maltase | 191. Units/ml |

Measurements were made at 340 nm, 38° C unless otherwise indicated, using a Gilford Recording Spectrophotometer (Model 2000). The sensitivity of the substrate in the assay was determined by measuring the rate of absorbance change after the addition of 10 μl of Moni-Trol ®IIX (Lot #XPT-540). The rate was determined after a 7 minute preincubation to ensure complete removal of the endogenous glucose in the Moni-Trol ® preparation.

Conductivity Measurements: The conductivity of solutions was determined with a Markson digital Conductivity Meter with automatic temperature compensation. (Model Electromark).

EXAMPLE I

Demonstration of the Synergistic Action of a Combination of Maltase and Yeast in the Production of Oligosaccharides Suitable for Use in an Amylase Assay It is well known from prior art that fermentation of oligosaccharide containing solutions with yeast removes $G_1$, $G_2$, and $G_3$ from the solution, and that larger oligosaccharides are fermented poorly if at all. These observations were confirmed using baker's yeast in these investigations. However, as shown in Table I, the simultaneous presence of baker's yeast and maltase in the oligosaccharide-containing solution gave the completely unexpected result that in addition to fermentation of $G_1$, $G_2$, and $G_3$, $G_4$ is removed by fermentation and is decreased to an acceptable level for amylase assays. Also there was a relative increase in the content of $G_5$, $G_6$ and $G_7$ which is also desirable.

It is also clearly evident from Table I that maltase alone will not significantly hydrolyze $G_4$ in the absence of yeast.

Table I

Treatment of corn syrup solutions with either maltase alone, yeast alone, or a combination of maltase and yeast.

| Additional treatment of corn syrup solution* | Relative peak heights of oligosaccharides after TLC separation** | | | | | | | |
|---|---|---|---|---|---|---|---|---|
| | $G_1$ | $G_2$ | $G_3$ | $G_4$ | $G_5$ | $G_6$ | $G_7$ | $G_8-G_n$ |
| Yeast alone | 0 | 0 | 0 | 30 | 20 | 15 | 8 | 100 |
| Maltase alone | 112 | 0 | 0 | 48 | 60 | 48 | 39 | 100 |
| Yeast and maltase in combination | 0 | 0 | 0 | 2 | 42 | 37 | 29 | 100 |

*Flasks containing 54 gm corn syrup, 150 ml of $H_2O$, 100 mg sodium azide, and 2 gm $KH_2PO_4$ were adjusted to pH 7.2 with KOH. Where indicated, 20 gm of baker's yeast or 153,000 units of maltase were added. The pH was maintained between 6.0 and 7.2 throughout the incubation at 30° C by the addition of KOH.
**The contents of the flask were examined for oligosaccharides after six days at 30° C. Relative peak heights before treatment of the corn syrup were 63, 52, 49, 31, 22, 9.2, 4.6, and 100 for $G_1, G_2 \ldots G_{8-n}$ respectively.

EXAMPLE II

Large Scale Preparation of Amylase Substrate 2.0 kg of corn syrup was dissolved in a total of 6 liters of $H_2O$. After the addition of 40 gm of $KH_2PO_4$, the pH was adjusted to 7.2 with KOH, and 2 gm of sodium azide were added. After bringing the temperature to 30° C, 454 gm of baker's yeast was added. Fermentation was allowed to proceed for 36 hours at which time complete removal of $G_1$, $G_2$, and $G_3$ was observed. The pH of the mixture was readjusted to pH 7.0 with KOH and $2 \times 10^6$ units of Peak I maltase and $4 \times 10^6$ units of Peak II maltase activity were added. (Peak I and Peak II maltase are fully defined in the above-identified copending application. It was subsequently determined that Peak I maltase activity was not effective in producing the synergistic effect described. However, the presence of Peak I maltase activity has no deleterious effect in the preparation). Fermentation was allowed to proceed for an additional 120 hours during which the pH was adjusted daily to 7.0 with KOH. The yeast was occasionally resuspended by gentle mixing.

Approximately 120 hours after the addition of maltase, the fermentation was terminated by the addition of HCl to the mixture to lower the pH to 4.0. The mixture was heated to 70° C during a 20 min. interval and chilled to room temperature.

The mixture was filtered after the addition of 15 gm/liter of Celite. Filtration yielded a clear, pale yellow solution. The solution was desalted by passage through Barnstead Company mixed bed deionizer cartridges (Catalog number D 8901). The eluate from the ion exchanger had a pH of 6.0, a conductivity of 1.65 micromhos, and was colorless and nearly odorless.

The preparation was lyophilized, yielding 785 grams of material.

EXAMPLE III

Demonstration of the Suitability of the Oligosaccharide Sample Prepared in Example II for use as an Amylase Substrate The suitability of the oligosaccharide for use as an amylase substrate was demonstrated by measurement of:

1. The blank rate in the absence of added amylase (Table II).
2. The response (sensitivity) of the assay system upon addition of a control serum sample containing amylase activity (Table II).
3. The correlation of the response of an amylase assay system employing the oligosaccharide fraction with the response of a standard method for the determination of amylase (Table III).

Table II

Evaluation of the suitability of the oligosaccharide fraction as a substrate for the assay of amylase with respect to blank rate and sensitivity.

| | Blank Rate | Sensitivity |
|---|---|---|
| Average | 2.78 | 68.9 |
| Number of determinations | 12 | 12 |
| Standard Deviation | 0.24 | 1.84 |
| Coefficient of Variations (%) | 8.8 | 2.6 |

*The blank rate and sensitivity are expressed as the change in milliabsorbance per minute
**The Sensitivity of detection of amylase activity was measured upon the addition of 10 ul of control serum (Moni-Trol$^R$ IIX).

From the initial absorbance change found upon the addition of substrate to the test reagent, $G_1$–$G_4$ contamination of the substrate was extremely low. From the data presented in Table II it is concluded that the substrate prepared by the procedure outlined above produces acceptable blank rates and acceptable sensitivities.

Table III

Correlation of the response of an amylase assay system employing the oligosaccharide fraction with the response of the Caraway iodometric procedure for the determination of amylase activity*

| Number of paired determinations | 52 |
|---|---|
| Correlation Coefficient | 0.998 |
| Correlation equation** | Y = 0.292 X + 30.7 |

*The activity of amylase was determined by the standard method of Caraway (McNair, R.D. in Standard Methods of Clinical Chemistry, edited by MacDonald, R.P. Academic Press, New York, 1970, pp. 183–188).
**Y = Caraway amylase units; X = IU/liter of amylase determined kinetically by the described analytical method using the oligosaccharide fraction.

Having now fully described the invention, it will be apparent to one of ordinary skill in the art that many changes and modifications can be made thereto without departing from the spirit or scope of the invention as set forth herein.

What is claimed as new and desired to be secured by letters patent of the United States:

1. A method for removing oligosaccharides in the range of $G_1$–$G_4$ from a solution containing the same, which comprises:
   simultaneously adding baker's yeast and the Peak II maltase enzyme characterized by hydrolyzing maltotetraose only about 1/100 as fast as maltose and maltopentaose only about 1/500 as fast as maltose derived from a strain of Saccharomyces, ATCC 20,488, to said solution;
   fermenting said yeast and maltose containing solution, whereby all of said $G_1$–$G_4$ oligosaccharides are removed by hydrolysis from the solution; and
   recovering said $G_1$–$G_4$ oligosaccharide free solution.

2. A method for preparing an oligosaccharide fraction containing $G_5$+ oligosaccharides, which comprises:
   adding to a natural extract derived from a grain or tuberous plant which contains a desired $G_5$+ oligosaccharide fraction as well as lower order saccharides which include a maltase inhibitory amount of glucose, both a yeast which is capable of fermenting maltose and glucose in said natural extract but which is incapable of fermenting the oligosaccharides of said desired $G_5$+ oligosaccharide fraction and a maltase which is capable of hydrolyzing maltotetraose; fermenting said admixture of said yeast and said maltase in said natural extract, whereby all of the lower order saccharides of said extract other than said desired $G_5+$ oligosaccharide fraction are hydrolyzed; and separating said yeast and maltase from said admixture, thereby obtaining said desired $G_5+$ fraction of oligosaccharides.

3. The method of claim 2, wherein said source solution is first treated with said yeast or said maltase alone.

4. The method of claim 2, wherein said yeast is baker's yeast or brewer's yeast.

5. The method of claim 2, wherein said yeast is a species of *Saccharomyces cerevisiae, Saccharomyces italicus* or *Saccharomyces uvarum*.

6. The method of claim 2, wherein said maltase hydrolyzes maltotetraose but not higher malto-oligosaccharides.

7. The method of claim 2, wherein said maltase is derived from *Saccharomyces cerevisiae* or from *Saccharomyces italicus*.

8. The method of claim 2, wherein said source solution is a natural extract derived from the enzymatic or acid hydrolysis of starch-containing materials.

9. The method of claim 2, wherein said source solution is corn syrup.

10. The method of claim 2, wherein from 0.0075 to 0.20 kg of yeast and from about $3 \times 10^5$ to $2 \times 10^6$ units of maltase activity per liter of said source solution is used.

11. The method of claim 2, wherein the temperature is maintained at from 20° to 35° C and the pH at from 6.0 to 7.5, and wherein said source solution is simultaneously treated with said yeast and said maltase for from 36 to 164 hours.

12. The method of claim 2, wherein after said treatment said maltase is denatured and said denatured maltase and yeast are removed from said source solution.

13. The method of claim 12, wherein said maltase and yeast are removed by adjusting the pH of the solution to from 2.0 to 4.0 rapidly heating it to from 70° to 75° C, cooling to from 0° to 25° and thereafter filtering the solution to remove said yeast and denatured maltase.

14. The method of claim 12, wherein after said removal of yeast and maltase, said solution is further purified by treatment with a mixed-bed ion-exchange resin and lyophilization.

15. A method for preparing a $G_5+$ oligosaccharide fraction, which comprises:

a. fermenting a solution containing from 0.05 to 0.40 kg of corn syrup per liter of $H_2O$, from 0.20 to 0.40 gm of sodium azide per liter of solution, and from 0 to about 15 gm of $KH_2PO_4$ per liter of solution, said solution being continually maintained at a pH of from 6.0 to 7.5 by the addition of NaOH or KOH and at a temperature of from 20° to 35° C, with from 0.0075 to 0.20 kg of baker's yeast per liter of solution for a period of from 18 to 36 hours, and adding from $3 \times 10^5$ to $2 \times 10^6$ units of maltase which is capable of hydrolyzing maltotetraose per liter of said solution for a period of from about 36 to 164 hours;

b. adjusting the pH of the solution to a value from 2.0 to 4.0, rapidly heating it to a temperature of from 70° to 75° C, and cooling it to from 0° to 25° C;

c. filtering said solution to remove denatured maltase and yeast; and d. passing said solution through a mixed-bed ion-exchange resin, and lyophilizing the effluent.

* * * * *